United States Patent [19]

Marsan et al.

[11] 4,392,862
[45] Jul. 12, 1983

[54] ABSORPTIVE DEVICE

[75] Inventors: Mario S. Marsan, Cincinnati, Ohio; Edward W. Hartwell, Lawrenceburg, Ind.

[73] Assignee: The Procter & Gamble Company, Cincinnati, Ohio

[21] Appl. No.: 239,821

[22] Filed: Mar. 2, 1981

[51] Int. Cl.³ .......................................... A61F 13/16
[52] U.S. Cl. .................................................. 604/366
[58] Field of Search .......... 128/284, 286, 287, 290 R, 128/290 W, 296; 604/365–366, 370, 372, 379, 385

[56] References Cited

U.S. PATENT DOCUMENTS

| | | |
|---|---|---|
| 3,047,444 | 7/1962 | Harwood ....................... 128/290 W |
| 3,063,454 | 11/1962 | Coates et al. .................. 128/290 W |
| 3,110,609 | 11/1963 | Bletzinger ...................... 128/290 W |
| 3,683,916 | 8/1972 | Mesek et al. . |
| 3,691,570 | 9/1972 | Gaines et al. . |
| 3,695,269 | 10/1972 | Malaney . |
| 3,779,246 | 12/1973 | Mesek et al. . |
| 3,886,942 | 6/1975 | Bernardin . |
| 3,987,792 | 10/1976 | Hernandez et al. . |
| 4,077,410 | 3/1978 | Butterworth . |
| 4,103,058 | 7/1978 | Humlicek . |

Primary Examiner—C. Fred Rosenbaum
Attorney, Agent, or Firm—Monte D. Witte; Fredrick H. Braun; Richard C. Witte

[57] ABSTRACT

Absorptive devices comprising a facing element, a support element, an absorbent core, and a backsheet. The facing element is a body fluid permeable, unbonded, carded web of resilient, hydrophobic fibers which has been affixed to the supporting element through the means of spaced apart regions of bonding. The supporting element is a body fluid permeable planer sheet compatible with and affixed to the facing element. The absorbent core must absorb and retain body fluids while the backsheet must be impermeable to such fluids. The four elements are superimposed one upon another in the order mentioned and are united in that position to form devices such as disposable diapers, sanitary napkins, incontinent pads and the like.

12 Claims, 2 Drawing Figures

ABSORPTIVE DEVICE

BACKGROUND OF THE INVENTION

1. Field of the Invention

This invention relates to absorptive devices. More particularly, it relates to devices used to absorb and retain body fluids such as diapers (especially disposable diapers), sanitary napkins, incontinent pads, surgical dressings, and the like.

2. Description of Background Art

Devices used to absorb body fluids are common items of commerce. For example, disposable diapers, sanitary napkins, and the like, having a body contacting surface, an absorbent core, and a generally impervious backsheet are well known to modern consumers.

One area in which research has been concentrated is that of the body contacting surface of the absorptive device. This surface must be soft to the touch, non-irritating to skin, and permeable to body fluids to such an extent that such fluids may rapidly pass therethrough into the absorbent core of the device. A variety of body contacting surfaces have been proposed. For example, Butterworth et al. in U.S. Pat. No. 4,077,410, issued Mar. 10, 1978, have suggested that a foamed melt of thermoplastic polymer can be extruded and then hot drawn to molecularly orient the resulting fibers to produce a body contacting surface of molecularly oriented fiber elements having a mean denier of not greater than 3 and a bulk density generally about 0.05 to about 0.15 g/cc. Malaney, in U.S. Pat. No. 3,695,269 issued Oct. 3, 1972 has suggested that a body contacting sheet can be made from non-absorbent fibers of from about 1 to about 15 denier, preferably from about 1.25 to about 3 denier, which have been formed into a web, bonded into a nonwoven fabric with conventional binder material, and then bulked in a conventional mechanical lofting apparatus.

SUMMARY OF THE INVENTION

The present invention is concerned with absorptive devices having improved body contacting surfaces. The absorptive device of this invention comprises four elements: a fluid permeable facing element, a fluid permeable support element, an absorbent core, and an impervious backsheet. The abosrbent core and backsheet are any of the conventional materials well known in the art. The support element is a fluid pervious sheet such as a nonwoven polyester or a monofilament scrim. The facing element is a low density, high bulk web of un-bounded thermoplastic fibers.

DETAILED DESCRIPTION OF THE INVENTION

The absorptive device of this invention comprises four elements: a fluid permeable facing element, a fluid permeable support element, an absorbent core, and a fluid impervious backsheet. Each element is superimposed one on the other to form the absorptive device.

Figure 2:
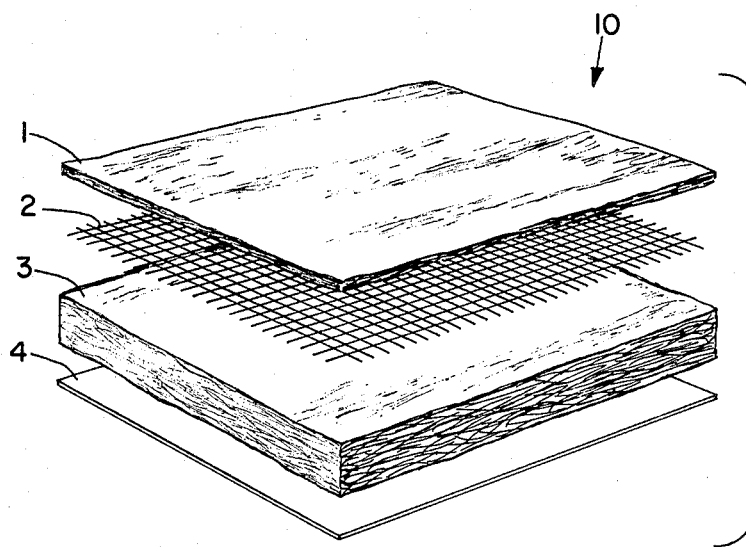
FIG. 2 is an exploded perspective view of a portion of an absorptive device of this invention showing the relative arrangement of the elements thereof. The thickness of certain elements has been exagerated for clarity.

FIG. 2 generally shows the relative positions of the four elements as they are arranged in the absorptive device.

In FIG. 2, the absorptive device is indicated generally by 10, the facing element by 1, the support element by 2, the absorbent core by 3, and the backsheet by 4. Facing element 1 is superimposed on support element 2 and is affixed thereto as hereinafter described. Support element 2 is superimposed on absorbent core 3. Absorbent core 3 is superimposed on backsheet 4.

Figure 1:
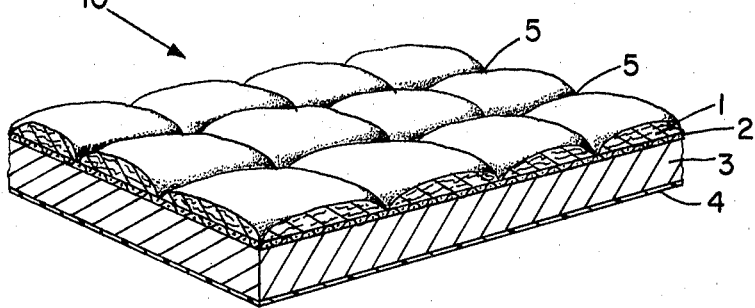
FIG. 1 is a perspective representation of a portion of an absorptive device of this invention.

FIG. 1 shows a portion of absorptive device 10 after it has been assembled. Facing element 1 is affixed to support element 2 by spaced apart regions of bonding 5. (In FIG. 1, these spaced apart regions of bonding 5 are represented as a network of lines of bonding forming squares. This is a preferred arrangement of spaced apart regions of bonding 5, but is not the only useful such arrangement.) This assembly of facing element 1 and support element 2 is then superimposed on absorbent core 3 and backsheet 4. The entire absorptive device structure is united by any convenient means appropriate for its intended use.

Facing element 1 comprises synthetic thermoplastic fibers. These fibers are resilient and, preferably, hydrophobic. Commercially available polyolefin and, preferably, polyester fibers are conveniently used. Other fibers useful herein include those formed from polyacrylamide, polystyrene, polyvinyl chloride, polyamide, polyvinylidene chloride, and the like. Since the absorptive devices are intended to be used in contact with human skin, it is preferred for comfort of the user that the fibers be from about 6 denier (0.0185 mm in diameter) to about 12 denier (0.037 mm), although fibers as fine as about 3 denier and as coarse as about 15 denier or more can be used. Fibers of 6 denier are quite suitable and are preferred.

In the manufacture of facing element 1, it is preferred that the fibers be as long as possible, since the longer the fiber, the fewer the number of bonds required to affix facing element 1 to support element 2. And, since the spaced apart regions of bonding are generally impervious to body fluids, the fewer the bonds, the more fluid permeable the combination of facing element 1 and support element 2. Crimped fibers having an uncrimped length of from about 7 centimeters to about 21 centimeters are suitable and preferred. These crimped fibers usually have a crimped length about 60% of their uncrimped length. Tows (bundles of long crimped or uncrimped fibers) can also be used in this invention.

Facing element 1 is a web of the hereinbefore described fibers. The term "web" as used herein means a carded or otherwise intangled network of fibers. Carded webs suitable for use in the practice of the present invention can have the fibers aligned substantially unidirectionally, although interwoven and cross-lapped webs can be used. Conventional carding machines can be used to prepare these webs. Examples of non-carded webs useful in this invention are airlaid webs and webs made by the well-known Rando-web process which uses equipment marketed by Rando Machine Corporation of Macedon, New York.

The webs should be formed without the use of chemical bonding agents, latex binders, or the like.

Facing element 1, prior to bonding to support element 2, should have a basis weight of from about 5 to about 50 grams per square meter and a density of from about 0.0002 to about 0.02 g/cc.

Facing element 1 is, by its nature, too weak to be used alone. It must be affixed to a suitable support element to form an assembly. Support element 2 can be any suitable planer material so long as it is permeable to body fluids and compatible with facing element 1 and absorbent core 3. In FIG. 2, support element 2 is illustrated as a scrim or open network of more or less continuous filaments such as monofilaments. For example, a scrim of nylon filaments coated with a thermoplastic polymer can be advantageously used. The exact parameters of the scrim are not important so long as it is freely fluid permeable, can be affixed to facing element 1, and has adequate strength for practical use.

Scrims are not the only materials which can be used for support element 2. Nonwoven fabrics such as those used as topsheets in disposable diapers also find use as support element 2. These materials must have the physical properties mentioned above.

A preferred support element is the polyester fabric sold under the tradename Reemay by E. I. DuPont de Nemours & Co. of Wilmington, Delaware. This material has a basis weight of about 20 grams per square meter and is about 0.2 millimeter thick.

Facing element 1 and support element 2 must be affixed to one another (united) by bonds in spaced apart regions of bonding to form an assembly. Since the combination of facing element 1 and support element 2 must be permeable to body fluids, the technique used to unite the two elements must be carefully selected so as not to unduly interfere with fluid passage. While chemical adhesives (such as hot melt adhesives) can be used, it is preferred that the two elements be united by thermal bonding such as that provided by the impulse heating of a conventional heat sealer.

The spaced apart regions of bonding can be in any convenient pattern such as lines or spots. In FIg. 1, the spaced apart regions of bonding 5 are shown in a useful rectalinear pattern. A preferred spaced apart region of bonding pattern is that of squares about 2.5 centimeters on a side. The total area occupied by the spaced apart regions of bonding should not exceed about 45% of the total surface area of the absorptive device.

Absorbent core 3 can be any convenient material which absorbs and retains body fluids. For example, creped cellulose wadding and airlaid comminuted wood pulp fibers such as those frequently used in disposable diapers are quite suitable. The absorbent core must, naturally, have sufficient absorptive capacity for the type and amount of body fluids expected to be encountered during the use of the absorptive device.

When the absorptive device will be used as a disposable diaper, the absorbent core can be airlaid comminuted wood pulp fibers and can have a basis weight of from about 20 to about 2000 grams per square meter and a density of from about 0.01 to about 1.0 g/cc.

Other absorbent cores that can be used are described in U.S. Pat. No. Re. 26,151 issued to Duncan et al. on Jan. 31, 1967, which is incorporated herein by reference. Still other suitable absorbent cores are shown in U.S. Pat. No. 3,860,003 which issued to Buell on Jan. 14, 1975, which is incorporated herein by reference.

Backsheet 4 can be any fluid impervious material commonly used with absorptive devices. For example, a thermoplastic film, such as polyethylene of from about 0.01 to about 0.035 millimeter thickness, is quite suitable. When the absorptive device is to be used as a disposable diaper, backsheets described in the hereinbefore incorporated patents to Duncan et al. and Buell can be used. Still other suitable backsheets are the breathable diaper backsheets as described in, for example, U.S. Pat. No. 3,881,489 issued to Hartwell on May 6, 1975 and U.S. Pat. No. 3,989,867 issued to Sisson on Nov. 2, 1976, both of which patents are incorporated herein by reference.

The four elements comprising the absorptive device of this invention are prepared in sizes and shapes convenient for the use intended. While all elements can have the same size and shape, they need not if the end use dictates otherwise.

To form the absorptive device of this invention, facing element 1 is superimposed on support element 2 and the two are affixed one to another as hereinbefore described. These two elements are superimposed on absorbent core 3 which is in turn superimposed on backsheet 4. The four superimposed elements can be united into a unitary article by any convenient means such as, for example, bonding by conventional hot melt adhesives placed about the margins of the absorptive device.

In another method of union, backsheet 4 is larger than the other elements and is folded over and about the other elements along at least two margins and is secured in that position by adhesive.

Thus far, the device of this invention has been described in a general way without regard to its specific intended end use. These absorptive devices, which comprise the four hereinbefore described elements, can be formed into a variety of useful articles by any of a variety of means. For example, the teachings of the hereinbefore incorporated patents to Duncan et al. and Buell can be used to make disposable diapers of the absorptive devices of this invention.

In order to more fully illustrate this invention, and not by way of limitation, the following example is presented.

EXAMPLE

A carded web having a basis weight of 15 grams per square meter and a density of 0.002 grams per cubic centimeter was formed from 6 denier, 15.2 centimeter long polyester fibers on a conventional carding machine. Sections of this web, 30.5 centimeters by 40.6 centimeters, were used as a facing element and were thermally bonded to a 30.5 centimeter by 45.7 centimeter support element. The support element was the hereinbefore described Reemay polyester fabic. Bonding was accomplished by heating the spaced apart regions of bonding to approximately 230° C. for approximately five seconds. The spaced apart regions of bonding were in the form of lines approximately 1.6 millimeters wide which formed squares approximately 2.5 centimeters on the side. An absorbent core approximately 30.5 centimeters by 40.6 centimeters by 0.25 centimeter thick, having a density of approximately 0.1 grams per cubic centimeter was formed from airlaid comminuted wood pulp fibers. The core was enclosed with an optional and conventional envelope of paper tissue. The assembly comprising the facing element and the support element was centered and superimposed on one surface of the absorbent core with the support element portion of the assembly adjacent the core. The longitudinally extending sections of the assembly were folded about the absorbent core and adhesively secured to the reverse side of the core. This assembly comprising the facing element, the support element, and the absorbent core was then superimposed and centered on an embossed 0.025 millimeter thick polyethylene backsheet. This backsheet, which was approximately 38 centimeters by 48 centimeters, had an apparent thickness of approximately 0.72 millimeters after embossing. The backsheet was folded about the associated facing element, supporting element, and absorbent core and adhesively affixed to the facing element surface and the absorbent core along the lateral margins thereof. The device was then folded into a conventional disposable diaper. The resulting disposable diapers performed satisfactory for their intended use.

What is claimed is:

1. An absorptive device comprising a facing element, a fluid permeable support element, an absorbent pad, and an impervious backsheet wherein said facing element comprises a fluid permeable, unbonded web of hydrophobic thermoplastic fibers, said fibers being from about 3 to about 15 denier; said web being formed without the use of bonding agents and having a density of from about 0.0002 to about 0.02 g/cc.; wherein said facing element is affixed to said support element in spaced apart regions of bonding by means selected from the group consisting of thermal bonding, hot melt adhesive bonding, and chemical adhesive bonding to form an assembly and said assembly is superimposed on said absorbent pad which is superimposed on said backsheet.

2. The absorptive devise of claim 1 wherein said fibers are polyester fibers.

3. The absorptive device of claim 1 or 2 wherein said facing element is affixed to said support element by thermal bonding.

4. A disposable diaper comprising a facing element, a fluid permeable support element, an absorbent pad, and an impervious backsheet wherein said facing element comprises a fluid permeable, unbonded web of hydrophobic thermoplastic fibers, said fibers being from about 3 to about 15 denier; said web being formed without the use of bonding agents and having a density of from about 0.0002 to about 0.02 g/cc.; wherein said facing element is affixed to said support element in spaced apart regions of bonding by means selected from the group consisting of thermal bonding, hot melt adhesive bonding, and chemical adhesive bonding to form an assembly and said assembly is superimposed on said absorbent pad which is superimposed on said backsheet.

5. The disposable diaper of claim 4 wherein said fibers are polyester fibers.

6. The disposable diaper of claim 4 or 5 wherein said facing element is affixed to said support element by thermal bonding.

7. The disposable diaper of claim 4 or 5 wherein said support element comprises a nonwoven fabric of polyester fibers.

8. The disposable diaper of claim 7 wherein said facing element is affixed to said support element by thermal bonding.

9. The disposable diaper of claim 4 or 5 wherein said support element comprises a monofilament scrim.

10. The disposable diaper of claim 9 wherein said facing element is affixed to said support element by thermal bonding.

11. The disposable diaper of claim 9 wherein said monofilament scrim is coated with thermoplastic polymer.

12. The disposable diaper of claim 10 wherein said monofilament scrim is coated with thermoplastic polymer.

* * * * *